United States Patent [19]

Iwataki et al.

[11] Patent Number: 4,515,729
[45] Date of Patent: May 7, 1985

[54] CYCLOHEXANE DERIVATIVES

[75] Inventors: Isao Iwataki; Kagari Fujita; Hisao Ishikawa; Hideo Hosaka; Kenichi Kohara, all of Kanagawa, Japan

[73] Assignee: Nippon Soda Company Limited, Tokyo, Japan

[21] Appl. No.: 461,000

[22] Filed: Jan. 26, 1983

Related U.S. Application Data

[63] Continuation of Ser. No. 269,468, Jun. 2, 1981, abandoned.

[30] Foreign Application Priority Data

Jun. 12, 1980 [JP] Japan ................................. 55-78397

[51] Int. Cl.³ .......................................... C07C 121/46
[52] U.S. Cl. .................................... 260/464; 564/300; 71/98; 71/103
[58] Field of Search ......................... 260/464; 564/300

[56] References Cited

U.S. PATENT DOCUMENTS

| 3,943,176 | 3/1976 | Dunbar et al. | 71/98 X |
| 3,989,737 | 11/1976 | Sawaki et al. | 71/108 X |
| 4,033,754 | 7/1977 | Sawaki et al. | 71/112 |
| 4,075,239 | 2/1978 | Sawaki et al. | 260/464 |
| 4,249,937 | 2/1981 | Iwataki et al. | 71/98 X |

Primary Examiner—Joseph Paul Brust
Attorney, Agent, or Firm—George B. Oujevolk

[57] ABSTRACT

A cyclohexane derivative having the formula

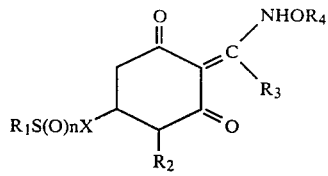

wherein
$R_1$ is $C_{1-4}$ alkyl or halo phenyl;
$R_2$ is $C_{1-3}$ alkyl or cyano group;
$R_3$ is $C_{1-4}$ alkyl;
$R_4$ is $C_{1-4}$ alkyl or $C_{1-4}$ alkenyl;
X is straight or branched chain $C_{1-4}$ alkylene; and
n is 0, 1 or 2, which possess herbicidal properties, and the process for its preparation.

1 Claim, No Drawings

CYCLOHEXANE DERIVATIVES

This is a continuation, of application No. 269,468 filed June 2, 1981, now abandoned.

The present invention relates to substituted cyclohexane-1,3-dione derivatives, to a process for the preparation thereof, and their uses as selective herbicides.

According to the present invention, there is provided a cyclohexane derivative having the formula

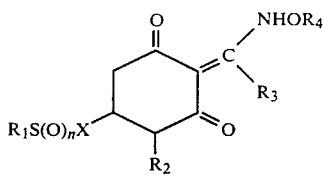

[I]

wherein
- $R_1$ is $C_{1-4}$ alkyl or halo phenyl;
- $R_2$ is $C_{1-3}$ alkyl or cyano group;
- $R_3$ is $C_{1-4}$ alkyl;
- $R_4$ is $C_{1-4}$ alkyl or $C_{1-4}$ alkenyl;
- X is straight or branched chain $C_{1-4}$ alkylene; and
- n is 0, 1 or 2.

The cyclohexane derivatives of the formula [I] have superior herbicidal activity and are particularly effective in the control of grass weeds, such as barnyard grass (*Echinochloa crus-galli*), blackgrass (*Alopecurus myosuroides*), crabgrass (*Digitaria sanguinalis*), wild oat (*Avena fatua*) and Johnsongrass (*Sorghum halepense*), and they hardly injure broad leaf crops such as beans, peas, radish, beets and cucumber which easily suffer phytotoxicity.

A part of the present inventors formerly discovered that some 5-alkylthio (sulfinyl or sulfonyl) alkyl cyclohexane-1,3-dione derivatives having a lower alkoxycarbonyl substitution at the 4-position have herbicidal activities, as disclosed in, for example, U.S. Pat. No. 4,249,937. The inventors have found that 5-alkylthio (sulfinyl or sulfonyl) alkyl cyclohexane-1,3-dione derivatives of formula [I] which possess $C_{1-3}$ alkyl or cyano group at the 4-position are not only as herbicidally active as the previous invention but also they exhibit improved effectiveness in the control of crabgrass than the foregoing cyclohexane-1,3-dione derivatives.

The compounds can be prepared in accordance with the following equation:

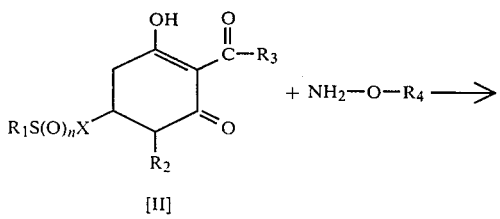

-continued

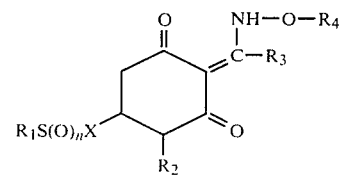

[I]

wherein $R_1$, $R_2$, $R_3$, $R_4$, X and n are as previously defined.

The above reaction can be conducted in an inert solvent.

As an inert solvent, acetone, diethyl ether, methyl alcohol, ethyl alcohol, isopropyl alcohol, benzene, tetrahydrofuran, chloroform, acetonitrile, dichloroethane, dichloromethane, ethyl acetate, dioxane, toluene, xylene and dimethyl sulfoxide may be used.

The reaction temperature may be from $-10°$ C. to the boiling point of the reaction solution, preferably from $10°$ to $60°$ C., and the reaction may be carried out for several hours or longer.

After the reaction has been completed, the solvent is, if necessary, removed and the reaction mixture is then extracted with an alkaline solution, or is poured into ice-cold water. The alkaline extract or the mixture with water is acidified with hydrochloric acid, and the crude product is isolated from the acidified mixture by extraction with solvent or by filtration.

If the product is crystalline, the crude product can be purified by recrystallization, and if the product is an oily substance, the crude product can be purified by distillation or isolation by column chromatography.

A chemical formula for the resulting purified compound can be assigned by means of an elemental analysis, NMR spectrum and IR spectrum.

It is expected that the compounds represented by the formula [I] exist in the following four tautomeric forms:

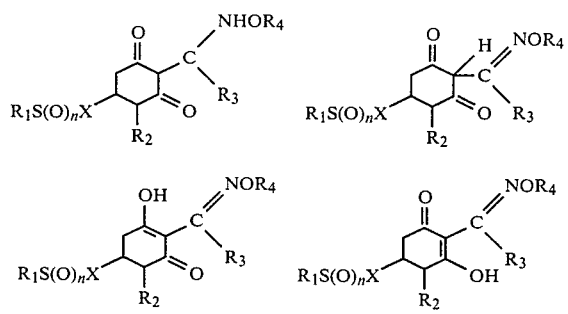

It is further expected that the compounds represented by the formula [II] exist in the following three tautomeric forms:

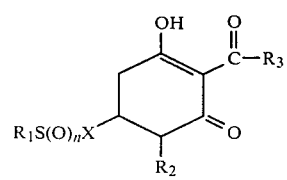

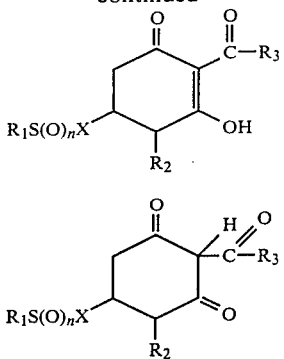

The starting material of the formula [II] can be prepared in accordance with the following equation wherein R is lower alkyl:

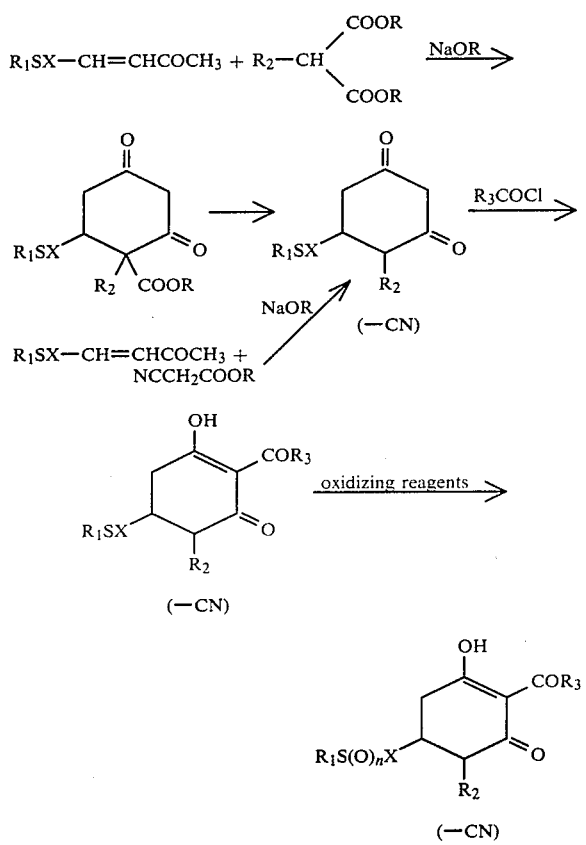

The following Examples illustrate the invention:

EXAMPLE 1

2-(1-ethoxyaminobutylidene)-5-(2-ethylthiopropyl)-4-methylcyclohexane-1,3-dione (Compound No. 1)

Into 10 ml of ethanol, 2.97 g of 2-butyryl-5-(2-ethylthiopropyl)-4-methylcyclohexane-1,3-dione was dissolved and 0.81 g of ethoxyamine was dropped thereto at 0° C. and the resulting solution was stirred at room temperature for 3 hours. After pouring the reaction solution into ice-cold water, the mixture was extracted with chloroform. The chloroform solution was washed with water and extracted with 1N-sodium hydroxide solution. The sodium hydroxide solution was acidified with 1N-hydrochloric acid and the acidified mixture was extracted with chloroform. The chloroform solution was washed with water and dried over anhydrous magnesium sulfate. The removal of chloroform by distillation under reduced pressure gave 3.0 g of the desired product as yellow oily material. Yield 88%, $n_D^{19.5}$ 1.5375.

EXAMPLE 2

2-(1-ethoxyaminobutylidene)-5-(2-ethylsulfinylpropyl)-4-methylcyclohexane-1,3-dione (Compound No. 2)

Into 20 ml of ethanol, 3.1 g of 2-butyryl-5-(2-ethylsulfinylpropyl)-4-methylcyclohexane-1,3-dione was dissolved and 0.61 g of ethoxyamine was dropped thereto at 0° C. and the resulting solution was stirred at room temperature for 3 hours. After completion of the reaction, the reaction solution was treated as in Example 1 to obtain 2.65 g of the desired compound as yellow oily material. Yield 74%, $n_D^{19}$ 1.5348.

EXAMPLE 3

2-(1-allyloxyaminopropylidene)-5-(2-ethylthiopropyl)-4-methylcyclohexane-1,3-dione (Compound No. 4)

Into 10 ml of ethanol, 2.8 g of 2-propionyl-5-(2-ethylthiopropyl)-4-methylcyclohexane-1,3-dione was dissolved and 1 g of allyloxyamine was dropped thereto at 0° C. and the resulting solution was stirred at room temperature for 3 hours. After pouring the reaction solution into ice-cold water and acidifying the mixture with hydrochloric acid, the mixture was extracted with chloroform. The chloroform solution was washed with water and dried over anhydrous magnesium sulfate. The removal of chloroform by distillation under reduced pressure gave 2.9 g of the desired product as yellow oily material. Yield 86%, $n_D^{18.5}$ 1.5389.

Inclusive of the above, compound embodying this invention which can be prepared in an analogeous manner are tabulated in Table 1.

TABLE 1

| Compound No. | $R_1S(O)_nX$ | $R_2$ | $R_3$ | $R_4$ | Physical Constant |
|---|---|---|---|---|---|
| 1 | $C_2H_5SCHCH_2-$<br>$\phantom{C_2H_5S}|$<br>$\phantom{C_2H_5SCH}CH_3$ | $-CH_3$ | $-C_3H_7$ | $-C_2H_5$ | $n_D^{19.5}$ 1.5375 |

TABLE 1-continued $$R_1S(O)_nX \text{ on cyclohexane ring with } R_2, =C(R_3)(NHOR_4), \text{ and two } =O$$

| Compound No. | $R_1S(O)_nX$ | $R_2$ | $R_3$ | $R_4$ | Physical Constant |
|---|---|---|---|---|---|
| 2 | C₂H₅SCHCH₂— with CH₃ branch, S=O | " | " | " | $n_D^{19}$ 1.5348 |
| 3 | (CH₃)₂CHSCH₂CH₂— | " | " | —CH₂CH=CH₂ | $n_D^{27}$ 1.5305 |
| 4 | C₂H₅SCHCH₂— with CH₃ branch | " | —C₂H₅ | " | $n_D^{18.5}$ 1.5389 |
| 5 | C₂H₅SO₂CHCH₂— with CH₃ branch | " | " | " | $n_D^{18.5}$ 1.5360 |
| 6 | C₂H₅SCHCH₂— with CH₃ branch | —CN | —C₃H₇ | —C₂H₅ | $n_D^{21}$ 1.5400 |
| 7 | Cl—C₆H₄—SCH₂CH₂— | | —CH₃ | " | " | $n_D^{25}$ 1.5711 |

As mentioned previously, the compounds possess superior herbicidal activity. The compounds may be applied directly to the soil as pre-emergence treatment or as post-emergence treatment to plant foliage, or they can be mixed intimately with soil. The preferred treatment is after emergence of the plant foliage and the compounds may be applied to soil or to plant foliage in amounts of 5 g or more per 10 are.

A herbicidal composition having the compound as its active ingredient may be formulated by mixing suitable carriers in a form generally used in agricultural chemicals, such as wettable powder, emulsifiable concentrate, granular formulation, water soluble powder and aerosol. As solid carriers, bentonite, diatomaceous earth, apatite, gypsum, talc, pyrophyllite, vermiculite and clay may be used. As liquid carriers kerosene, mineral oil, petroleum, solvent naphtha, benzene, xylene, cyclohexane, cyclohexanone, dimethylformamide, alcohol and acetone may be used. A surface active agent may also be added, in order to give a homogeneous and stable formulation.

The compounds can be applied admixed with other chemicals, which are used in agronomic and horticultural management and which are compatible with such compounds. Such chemicals can be, but are not restricted to, the classes of chemical commonly known as plant nutrients, fertilizers, insecticides, acaricides, fungicides, herbicides and nematocides.

For admixture of the compound with known herbicides, the use is recommended of triazine derivatives such as simazine, propazine and prometryn, carbamate derivatives such as phenmedipham, urea derivatives such as metabenzthiazuron and linuron, and heterocyclic compounds such as pyrazon and lenacil.

The concentration of the active ingredient in a herbicidal composition may vary according to type of formulation, and the concentration is, for example, in the range of 5–30 weight percent, preferably 10–20 weight percent, in wettable powder; 5–70 weight percent, preferably 20–60 weight percent, in emulsifiable concentrates; and 0.5–30 weight percent, preferably 1–10 weight percent, in granular formulation.

A wettable powder or an emulsifiable concentrate thus produced may be diluted with water to a specified concentration and used as a liquid suspension or a liquid emulsion for treating soils or plant foliage. Further, a granular fromulation may be directly used for soil or foliage treatment.

Non-limiting examples of herbicidal compositions are illustrated by the following tests:

EXAMPLE 4

Wettable Powder

| | Parts by weight |
|---|---|
| Compound No. 4 | 20 |
| White carbon | 20 |
| Diatomaceous earth | 52 |
| Sodium alkylsulfate | 8 |

These are mixed homogeneously and reduced to fine particles to provide a wettable powder containing 20% of active ingredient. In use, it is diluted to a desired concentration with water, and is sprayed as a suspension.

EXAMPLE 5

Emulsifiable Concentrate

|  | Parts by weight |
| --- | --- |
| Compound No. 2 | 40 |
| Xylene | 35 |
| Dimethylformamide | 15 |
| Polyoxyethylene phenylether | 10 |

These are mixed together to provide an emulsifiable concentrate containing 40% of the active ingredient. In use, it is diluted to a desired concentration with water, and is sprayed as an emulsion.

EXAMPLE 6

Granular Formulation

|  | Parts by weight |
| --- | --- |
| Compound No. 4 | 7 |
| Talc | 38 |
| Clay | 38 |
| Bentonite | 10 |
| Sodium alkylsulfate | 7 |

These are mixed homogeneously and reduced to fine particles. The fine particles are made into granules, each having a diameter in the range of 0.5–1.0 mm, to provide a granular formulation containing 7% of the active ingredient. In use, it is directly applied.

The herbicidal effects of compounds are illustrated by the following tests:

Test 1

Seeds of crabgrass, wild oat, lamb's-quarters and pig weed were planted in each pot having a surface area of 100 cm$^2$. When the plants were grown to 2–5 leaves stage, an aqueous emulsion, prepared by diluting an emulsifiable concentrate with water to a specified concentration, was sprayed on the foliage of the test plants at a rate of 100 l/10 are, and the pots were kept in a green-house. Fourteen days after spraying, the degree of damage to the each plant was observed and evaluated on the scale of values of 0–10, which has the following meanings:

0: no effect
2: partial plant slightly injured
4: plant slightly injured
6: plant moderately injured
8: plant severely injured
10: plant completely killed;
1, 3, 5, 7 and 9 mean the intermediate degree between 0 and 2, 2 and 4, 4 and 6, 6 and 8, and 8 and 10 respectively.

The results are shown in Table 2.

TABLE 2

| Compound No. | Application Rate (g/10 are) | Degree of Damage | | | |
| --- | --- | --- | --- | --- | --- |
| | | crabgrass (5 leaves stage) | wild oat (2–3 leaves stage) | lamb's-quarters (3 leaves stage) | pig weed (3 leaves stage) |
| 1 | 50 | 10 | 10 | 0 | 0 |
|  | 25 | 10 | 10 | 0 | 0 |
| 2 | 50 | 10 | 10 | 0 | 0 |
|  | 25 | 10 | 10 | 0 | 0 |
| 3 | 50 | 10 | 10 | 0 | 0 |
|  | 25 | 10 | 10 | 0 | 0 |
| 4 | 50 | 10 | 10 | 0 | 0 |
|  | 25 | 8 | 10 | 0 | 0 |
| 5 | 50 | 10 | 10 | 0 | 0 |
|  | 25 | 9 | 9 | 0 | 0 |
| 6 | 50 | 9 | 9 | 0 | 0 |
| *Comparative Compound | 50 | 10 | 10 | 0 | 0 |
|  | 25 | 4 | 10 | 0 | 0 |

*Comparative Compound

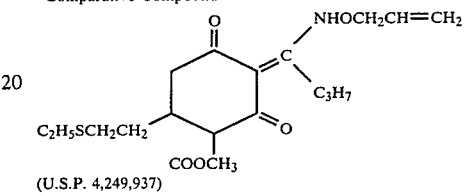

(U.S.P. 4,249,937)

Test 2

Seeds of soyabean, corn, sugar beet and cotton were planted in each pot having a surface area of 100 cm$^2$. When the plants were grown to 1–2 leaves stage, an aqueous emulsion, prepared by diluting an emulsifiable concentrate with water to the specified concentration, was sprayed on the foliage of the test plants at a rate of 100 l/10 are, and the pots were kept in a green-house. Three weeks after spraying, the degree of damage to the each plant was observed and evaluated on the same scale in Test 1.

The results are shown in Table 3.

TABLE 3

| Compound No. | Application Rate (g/10 are) | Degree of Damage | | | |
| --- | --- | --- | --- | --- | --- |
| | | corn | soyabean | sugar beet | cotton |
| 1 | 100 | 10 | 0 | 0 | 0 |
|  | 50 | 10 | 0 | 0 | 0 |
| 2 | 100 | 10 | 0 | 0 | 0 |
|  | 50 | 10 | 0 | 0 | 0 |
| 3 | 100 | 10 | 0 | 0 | 0 |
|  | 50 | 10 | 0 | 0 | 0 |
| 4 | 100 | 10 | 0 | 0 | 0 |
|  | 50 | 10 | 0 | 0 | 0 |
| 5 | 100 | 10 | 0 | 0 | 0 |
|  | 50 | 10 | 0 | 0 | 0 |
| 6 | 100 | 10 | 0 | 0 | 0 |
|  | 50 | 10 | 0 | 0 | 0 |
| *Comparative Compound | 100 | 10 | 0 | 0 | 0 |
|  | 50 | 8 | 0 | 0 | 0 |

*Comparative compound is the same with Test 1.

What we claim is:
1. A compound having the structural formula

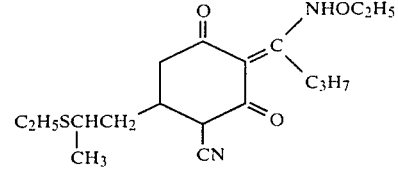

also known as 2-(1-ethoxyaminobutylidene)-5-(2-ethylthiopropyl)-4-cyanocyclohexane-1,3-dione.